United States Patent [19]

Benjes et al.

[11] Patent Number: 4,599,168

[45] Date of Patent: * Jul. 8, 1986

[54] APPARATUS FOR TREATMENT OF WASTE WATER HAVING SELECTIVE RECYCLE CONTROL

[75] Inventors: Henry H. Benjes, Overland Park; Valery N. Wahbeh, Leawood; John R. Stukenberg, Overland Park, all of Kans.

[73] Assignee: Bacardi Corporation, San Juan, P.R.

[*] Notice: The portion of the term of this patent subsequent to Jan. 19, 1999 has been disclaimed.

[21] Appl. No.: 685,201

[22] Filed: Dec. 20, 1984

Related U.S. Application Data

[63] Continuation of Ser. No. 510,361, Jul. 1, 1983, abandoned, which is a continuation-in-part of Ser. No. 347,665, Feb. 10, 1982, abandoned, which is a continuation of Ser. No. 187,470, Sep. 15, 1980, abandoned.

[51] Int. Cl.$^4$ .............................................. C02F 3/10
[52] U.S. Cl. ................................ 210/151; 210/180; 210/188; 210/195.3; 210/197; 210/218
[58] Field of Search ............... 210/601, 603, 605, 610, 210/612, 613, 614, 615–618, 630, 631, 150, 151, 96.1, 149, 180, 188, 195.3, 197, 218; 435/167

[56] References Cited

U.S. PATENT DOCUMENTS

| Re. 20,451 | 7/1937 | Ornstein | 210/180 |
|---|---|---|---|
| 624,985 | 5/1899 | Scott-Moncrieff | 210/180 |
| 699,345 | 5/1902 | Provost, Jr. | 210/180 |
| 1,797,157 | 3/1931 | Rudolfs | 210/180 |
| 1,799,444 | 4/1931 | Sperr, Jr. | 210/180 |
| 1,925,679 | 9/1933 | Skinner | 210/180 |
| 1,932,214 | 9/1921 | Peck | 210/180 |
| 1,997,252 | 4/1935 | Fischer | 210/180 |
| 2,029,702 | 2/1936 | Buswell et al. | 210/180 |
| 2,190,598 | 2/1940 | Fischer | 210/612 |
| 2,308,866 | 1/1943 | Dekema | 210/617 |
| 2,360,769 | 10/1944 | Gavett | 210/180 |
| 2,364,298 | 12/1944 | Kamp | 210/150 |
| 2,516,076 | 7/1950 | Schlenz | 210/180 |
| 2,553,228 | 5/1951 | Yonner | 210/180 |
| 2,640,027 | 5/1953 | McMamee | 210/180 |

(List continued on next page.)

FOREIGN PATENT DOCUMENTS

| 2905371 | 8/1979 | Fed. Rep. of Germany | 210/180 |
|---|---|---|---|
| 2337576 | 11/1971 | France | 210/180 |
| 801144 | 9/1958 | United Kingdom | 210/603 |

OTHER PUBLICATIONS

Published French Patent Application No. 77 30421, Witt et al, 5/26/1978.
Coulter, J. B. et al., "Anarobic Contact Process for Sewage Disposal", Sewage and Industrial Wastes, vol. 29, 1957, pp. 463–477.

(List continued on next page.)

Primary Examiner—Ernest G. Therkorn
Attorney, Agent, or Firm—Litman, Day & McMahon

[57] ABSTRACT

An apparatus is provided for treatment of organic contaminant containing waste water such that the oxygen demand of the waste water is reduced and methane is produced. The apparatus comprises an anaerobic digester or filter. The digester is packed with a media which provides a substantial growth surface area to microorganisms contained within the digester. The digester also includes recirculation means whereby fluid in the digester below the media is recirculated directly to an upper portion of the digester. Furthermore, the digester has effluent overflow outlets which outlets include a trap to prevent oxygen from entering the digester from the atmosphere. Fluid to be treated in the digester enters the upper portion thereof, passes downwardly through the media, is recirculated by the recirculating means to an upper portion of the digester, and exits the digester after treatment by the microorganisms therein through the outlets. The recirculating means may be selectively adjusted to vary flow in different portions of the digester.

A process is also provided for removing sulfur from the digester to prevent "sulfide" poisoning.

10 Claims, 9 Drawing Figures

U.S. PATENT DOCUMENTS

| | | | |
|---|---|---|---|
| 2,661,332 | 12/1953 | Mortenson | 210/180 |
| 2,786,025 | 3/1957 | Lamb et al. | 210/180 |
| 2,875,151 | 2/1959 | Davidson | 210/180 |
| 2,881,137 | 4/1959 | Logan | 210/180 |
| 2,889,929 | 6/1959 | Kivell | 210/180 |
| 3,010,581 | 11/1961 | Knapp et al. | 210/180 |
| 3,112,261 | 11/1963 | Porter | 210/180 |
| 3,168,465 | 2/1965 | Krause et al. | 210/180 |
| 3,188,288 | 6/1965 | Smith | 210/180 |
| 3,202,285 | 8/1965 | Williams | 210/180 |
| 3,259,566 | 7/1966 | Forpey | 210/180 |
| 3,275,147 | 9/1966 | Gilde | 210/180 |
| 3,338,826 | 8/1967 | Kramer | 210/163 |
| 3,356,609 | 12/1967 | Bruemmer | 210/610 |
| 3,383,309 | 5/1968 | Chandler | 210/180 |
| 3,402,103 | 9/1968 | Amberg | 210/615 |
| 3,468,794 | 9/1969 | Amero | 210/180 |
| 3,607,736 | 9/1971 | Miyaji | 210/180 |
| 3,709,364 | 1/1973 | Savage | 210/180 |
| 3,711,392 | 1/1973 | Metzger | 210/603 |
| 3,724,542 | 1/1973 | Hamilton | 210/180 |
| 3,773,179 | 11/1973 | Hurst | 210/194 |
| 3,829,377 | 8/1974 | Hashimoto | 210/180 |
| 3,835,038 | 9/1974 | Heaney | 210/180 |
| 3,838,199 | 9/1974 | Coe | 210/603 |
| 3,847,803 | 11/1974 | Fisk | 210/180 |
| 3,926,795 | 12/1975 | Saldick | 210/180 |
| 3,957,632 | 5/1976 | Knopp et al. | 210/180 |
| 3,977,965 | 8/1976 | Tholander et al. | 210/180 |
| 3,981,800 | 9/1976 | Ort | 210/180 |
| 3,981,803 | 9/1976 | Coulthard | 210/180 |
| 4,026,802 | 5/1977 | Akae | 210/180 |
| 4,040,953 | 8/1977 | Ort | 210/180 |
| 4,043,936 | 8/1977 | Francis et al. | 210/180 |
| 4,351,729 | 9/1982 | Witt | 210/617 |

OTHER PUBLICATIONS

McCarty, P. L., "Anaerobic Waste Treatment Fundamentals, Part I–Chemistry and Microbiology; Part II–Environmental Requirements and Control; Part III–Toxic Materials and Their Control; Part IV–Process Design", Public Works, Sep., Oct., Nov., Dec., respectively, 1964.

McCarty, P. L. "Anaerobic Treatment of Soluble Wastes", paper presented at special lecture series on Advances in Water Quality Improvement: The University of Texas, Austin, Texas, pp. 336 to 553, Apr. 4–7, 1966.

Young, J. C.-McCarty, P. L., "The Anaerobic Filter for Waste Treatment", Journal Water Pollution Control, Federation, 41, 5, pp. R160,R175, May, 1969.

Dague, R. R., McKinney, R. E. & Pfeffer, J. T., "Solids Retention in Anaerobic Waste Treatment Systems", Journal Water Pollution Control Federation, 42, 2, part 2, pp. R29 to R46, Feb. 1970.

Lovan, C. R., Forle, E. G., "The Anaerobic Filter for the Treatment of Brewery Press Liquor Waste", 26th *Purdue Industrial Waste Conference, pp. 1074 to 1086, 1971.*

Taylor, D. W., "Full Scale Anaerobic Filter Evaluation", Third National Symposium on Food Processing Wastes, pp. 151 to 162, EPA-R2-72-018, Nov. 1972.

Arora, H. C., "Treatment of Vegetable Tanning Effluents by the Anaerobic Contact Filter Process", *Water Pollution Control,* , vol. 74, 5, pp. 594 to 597, 1974.

Mueller, J. A., Mancini, J. C., "Anaerobic Filter-Kinetics and Application", 30th Purdue Industrial Waste Conference, pp. 423 to 447, 1975.

Chian, E. S. K., et al., "Removal of Heavy Metals From a Fatty Acid Waste Water With Completely Mixed Anaerobic Filter", 32nd *Purdue Industrial Waste Conference,* pp. 920 to 928, 1977.

Sachs, E. F., et al, "Anaerobic Treatment of Synthesized Organic Chemical Pharmaceutical Waste", 33rd Purdue Industrial Waste Conference, pp. 507 to 514, 1978.

L. Van den Berg. et al, "Comparison Between Up and Downflow Anaerobic Fixed Film Reactors of Varying Surface Volume Ratios for the Treatment of Bean Blanching Waste", 34th *Purdue Industrial Waste Conference,* 1979, pp. 319 to 325.

Witt; E. R., et al., "Full Scale Anaerobic Filter Treats High Strength Waste", 34th *Purdue Industrial Waste Conference,* pp. 229 to 234, 1979.

Dague, R. R., et al., "Anaerobic Filter Treatment of Recycle From Thermal Sludge Conditioning and Dewatering", 53rd Annual Conference of the WPCP, Las Vegas, Nevada, pp. 11 to 30, Sep. 1980.

Crawford, G. V., et al., "Anaerobic Treatment of Thermal Conditioning Liquors", Journal of WPCP, vol. 54, pp. 1458 to 1496, Nov. 11, Sep. 1980.

Van Den Berg, L., et al., "Anaerobic Waste Treatment Efficiency Comparisons Between Fixed Film Reactors, Contact Digestors and Fully Mixed Continuously Fed Digesters", 35th *Purdue Industrial Waste Conference,* May, 1980, pp. 788 to 793.

Van den Berg, L., et al., "Effect of Type of Waste on Performance of Anaerobic Fixed Film and Upflow Sludge Bed Reactors", *Industrial Waste Conference at Purdue,* May, 1981, pp. 1 to 19.

Van den Berg, L., et al., "Potential Use of Anaerobic Processes for Industrial Waste Treatment", Anaerobic Waste Water Treatment and Energy Recovery in Pittsburg, Nov., 1981, pp. 1 to 26.

Kennedy, K. J. et al., "Effects of Temperature and Overloading on the Performance of Anaerobic Fixed Film Reactors", 36th *Industrial Waste Conference at Purdue,* 1981, pp. 1 to 16.

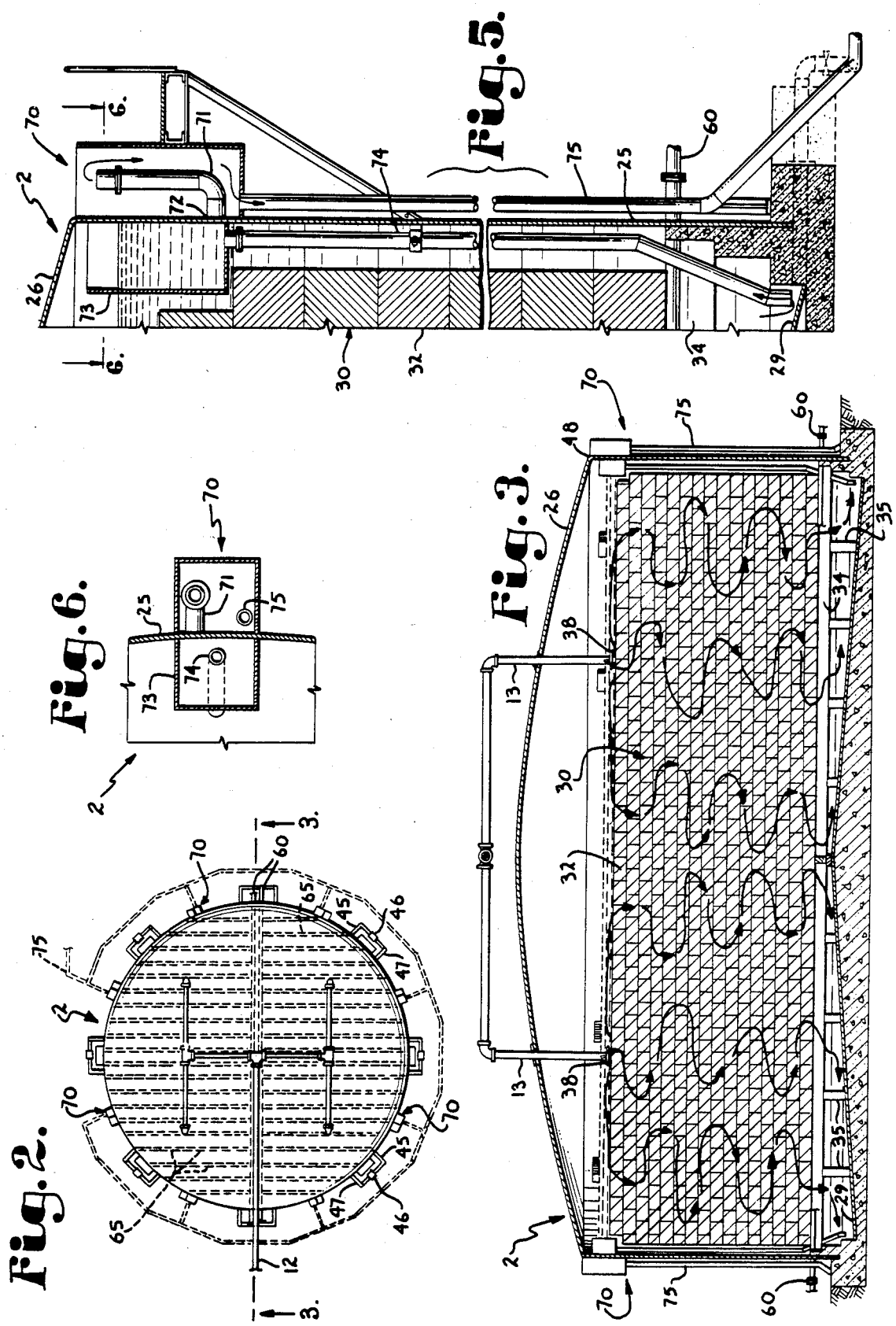

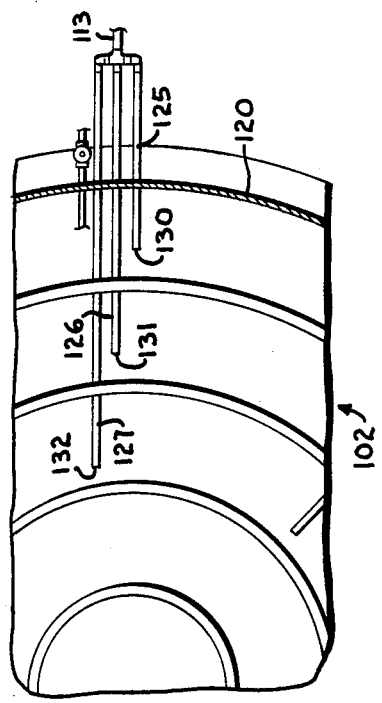
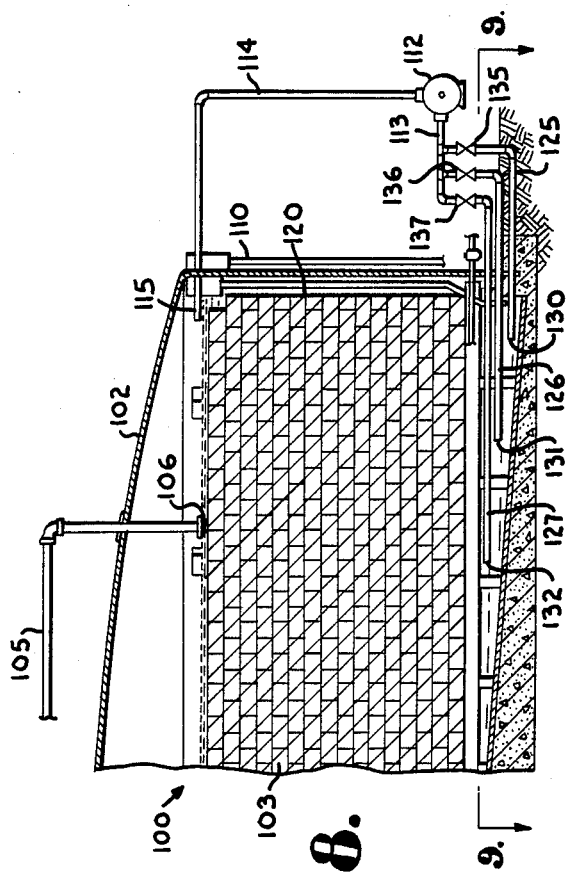
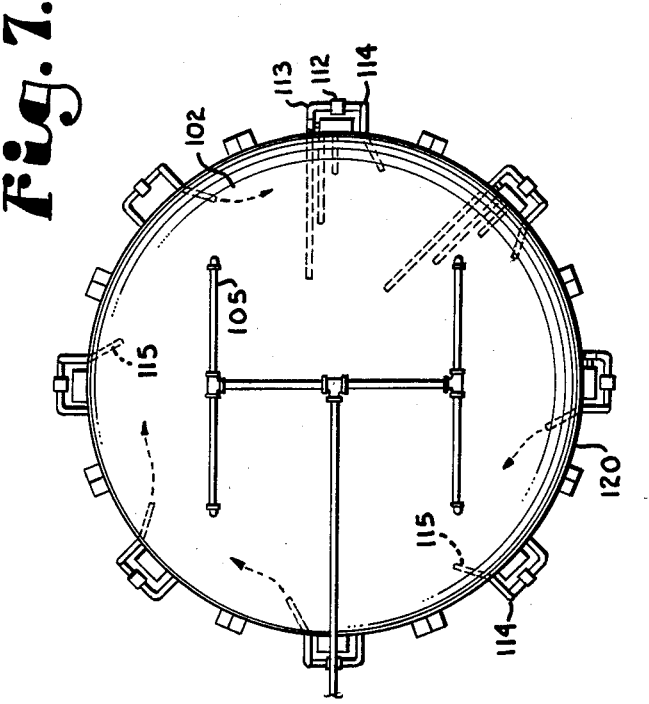

APPARATUS FOR TREATMENT OF WASTE WATER HAVING SELECTIVE RECYCLE CONTROL

CROSS-REFERENCE TO RELATED APPLICATIONS

The present application is a continuation of Ser. No. 510,361, filed July 1, 1983, now abandoned, which is a continuation-in-part of Ser. No. 347,665, filed Feb. 10, 1982, now abandoned, which is a continuation of Ser. No. 187,470, filed Sept. 15, 1980, now abandoned.

The present application is related to Ser. No. 187,551, filed Sept. 15, 1980, now U.S. Pat. No. 4,311,593.

BACKGROUND OF THE INVENTION

The present invention relates to treatment of waste water or sewage so as to remove impurities therefrom, in particular to the removal of oxygen demanding impurities and the production of methane therefrom.

Historically there have been a great number of devices and processes for removing impurities from the waste water so as to improve the quality thereof. Such devices have included clarifiers and digesters, and such processes have included both aerobic and anaerobic processes. Anaerobic processes are commonly referred to as filter and contact processes. In a typical anaerobic filter process the waste water is directed upwardly through a filter vessel (digester) with microorganisms therein and is thereafter passed through a degasifier and into a settling basin. An underflow from the settling basin is then returned to the filter vessel. In the anaerobic contact process waste water is injected into a vessel and agitated in contact with sludge containing microorganisms. Effluent leaving the contact vessel is passed through a degasifier and into a settling tank. Heavier sludge falls to the bottom of the settling tank and is recirculated to the contact vessel.

There are a large number of industries which, because of the nature of the product thereof, produce a waste water solution which is very high in organic constituents and is generally unacceptable for disposition in a lake, a river or the like because of the high oxygen demand associated therewith. In particular, environmental laws and regulations are becoming increasingly stringent in requiring the removal of chemical and biological oxygen demanding substances (COD and BOD) from waste water before such water is allowed to flow into public waterways. An example of such a waste water is the effluent from processes wherein molasses or the like is fermented and distilled in the production of alcoholic beverages or ethanol for the use in gasohol, such waste being commonly referred to as slops, spent grains, or mostos. The mostos, which is substantially underflow produced in the distillation process, typically has certain elements such as yeast already removed therefrom, however, same will typically have a very high oxygen demand.

OBJECTS OF THE INVENTION

Therefore, the objects of the present invention are to provide an apparatus for the removal of organic contaminants from waste water, especially mostos or the non-distilled remains from a fermentation and distillation process, and to produce methane by anaerobic action of microorganisms; to provide such an apparatus wherein the apparatus contains a large surface area type media suitable for growth of microorganism biomass therein; to provide such an apparatus wherein waste water after passing downwardly through the media in combination with a microorganism biomass contained therein is recirculated directly from a bottom portion of the digester to an upper portion of the digester by recirculating means; to provide such an apparatus wherein the recirculation flow can be selectively varied from different locations within the digester; to provide such an apparatus wherein the fluid being recirculated can be selectively and variably withdrawn from circumferentially and/or radially spaced locations within the bottom of the digester to control flow of fluid through sections of the digester above the locations of fluid withdrawal; to provide such an apparatus having an inlet located such that influent waste water is distributed in an upper portion of the digester; to provide such an apparatus having an effluent overflow outlet which is provided with a trap to ensure that oxygen does not enter the digester and that gases within the digester do not mix with the atmosphere; to provide such an apparatus wherein the influent waste water enters the top of the digester, passes through the media, is recirculated back to the top of the digester generally for several recirculations, and then exits the digester after having been acted upon by the microorganisms to substantially reduce the biological oxygen demanding material therein and so as to produce methane; to provide such an apparatus including suitable systems for selectively adding nutrients and/or buffering solution to the waste water so as to maximize activity of the microorganisms within the digester; to provide such an apparatus including collection and holding means for removing methane from the top of the digester and storing same; to provide such an apparatus having methane recirculation means such that the methane may be directed to a lower portion of the digester so as to agitate large accumulations of microorganism biomasses therein, especially in the vicinity of a floor of the digester, and to prevent plugging of the media; to provide such an apparatus including a recirculation system for methane released therein and a desulfurizer located operably in such recirculation system to provide for removal of sulfides from the digester by stripping using such release methane; to provide such an apparatus which is economical to manufacture, efficient in use, and which is particularly adapted for the proposed usage thereof.

Other objects and advantages of this invention will become apparent from the following description taken in connection with the accompanying drawings wherein are set forth by way of illustration and example, certain embodiments of this invention.

SUMMARY OF THE INVENTION

An apparatus is provided for treatment of waste water containing organic contaminants. In particular, preferably both the oxygen demand of the waste water is reduced and methane is produced while the waste water is in the apparatus. The apparatus comprises an anaerobic digester or filter. The digester is packed normally at least in an intermediate portion thereof with a media which provides a substantial surface area to microorganisms contained within the digester. The digester also includes recirculation means whereby fluid in a lower portion of the digester, especially below the media, is recirculated directly to an upper portion of the digester, such that microorganism biomass contained in such fluid is transferred to the digester upper portion.

The recirculation means, normally a pump, includes control means for selectively varying or adjusting the flow through the pump so that the recirculation waste water ratio to inlet waste water can be varied. The suction for the recirculation means converges from multiple inlets which are radially spaced from each other in a generally horizontal plane beneath the media in the digester. Valves or the like are provided on each recirculation means suction to allow selective control of the flow from each of the individual suction line intakes or inlets. In addition, where several spaced recirculation means or devices are utilized, the control means may be utilized to modify the amount of fluid withdrawn from one lower portion of the digester as compared to another radially or circumferentially spaced lower portion so as to be able to vary flow through the media both radially and circumferentially across a horizontal cross-section of the digester. In this manner flow of waste water down through the digester may be varied in accordance with blockage of the media by microorganism growth or to modify flow rates of waste water through different sectors of the digester wherein microorganism activity varies, so as to make optimal use of high activity regions.

Furthermore, the digester includes effluent overflow outlets, which outlets include a trap to prevent oxygen from entering the digester from the atmosphere and escape of methane from the digester.

Waste water fluid to be treated in the digester enters the upper portion thereof, passes downwardly through the media, is recirculated by the recirculating means to an upper portion of the digester, and exits the digester after treatment by the microorganisms therein through the outlet of the digester. Preferably, the recirculation rate, as well as the variation in the amount of recirculation withdrawn from a particular region of the digester, can be selectively controlled to adjust for digester conditions and to maximize the digesting process.

Collection and storage means are provided to withdraw methane produced in the digester therefrom. The methane may be stored, burnt to provide heat, and/or selectively returned to the digester in the lower portion thereof whereat same is dispensed preferably under pressure so as to agitate biomasses of microorganisms in the digester, especially near a floor thereof thereby facilitating interaction between the fluid and the microorganisms. Distributing means are provided to distribute the methane in a lower portion of the digester. Other agitation agents, such as recycled digester effluent under pressure may be selectively distributed by the distribution means so as to function as an agitation agent within the digester.

The methane recirculation system also includes a desulfurization vessel through which the methane returning to the digester may be selectively passed. In this manner the sulfur, especially in the form of hydrogen sulfide, in the digester, may be removed therefrom by circulating methane, including bubbling the methane through the fluid in the digester and subsequently through the desulfurization vessel, such that the methane tends to strip the sulfur from the digester and deposit the stripped sulfur in the vessel. This process allows control over the amount of sulfur in the digester to prevent or reduce "sulfide" poisoning therein and consequent reduction in activity of the microorganisms.

Also, the apparatus includes addition means for adding nutrients for the microorganisms to the digester influent and/or to add buffering solution thereto in order to control pH within the digester.

The drawings constitute a part of this specification and include exemplary embodiments of the present invention and illustrate various objects and features thereof.

BRIEF DESCRIPTION OF THE DRAWINGS

FIG. 2 is a top plan view of the digester including piping associated therewith.

FIG. 3 is a cross-sectional view of the digester taken along line 3—3 of FIG. 2.

FIG. 5 is a fragmentary and enlarged vertical cross-sectional view of the digester showing a side thereof with an associated overflow.

FIG. 6 is a fragmentary horizontal cross-sectional view of the digester showing the overflow as seen in FIG. 5.

FIG. 7 is a top plan view of a modified embodiment of a digester according to the present invention showing certain interior details of the digester in phantom.

FIG. 8 is an enlarged and fragmentary, side elevational and cross-sectional view of the digester shown in FIG. 7.

FIG. 9 is an enlarged and fragmentary cross-sectional view of the digester taken along line 9—9 of FIG. 8.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
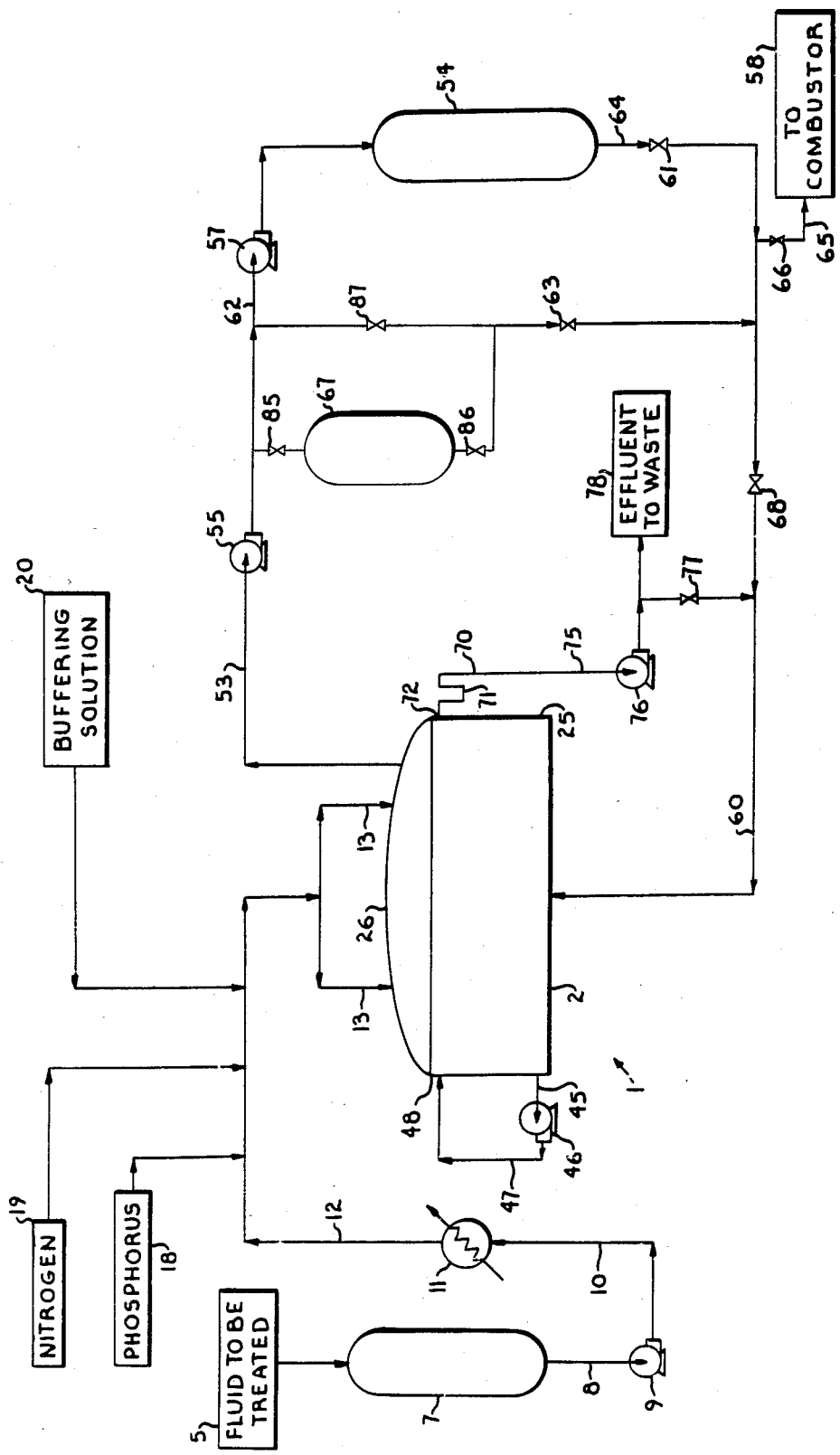
FIG. 1 is a schematic diagram of an apparatus performing the process of the present invention including a digester.
Figure 4:
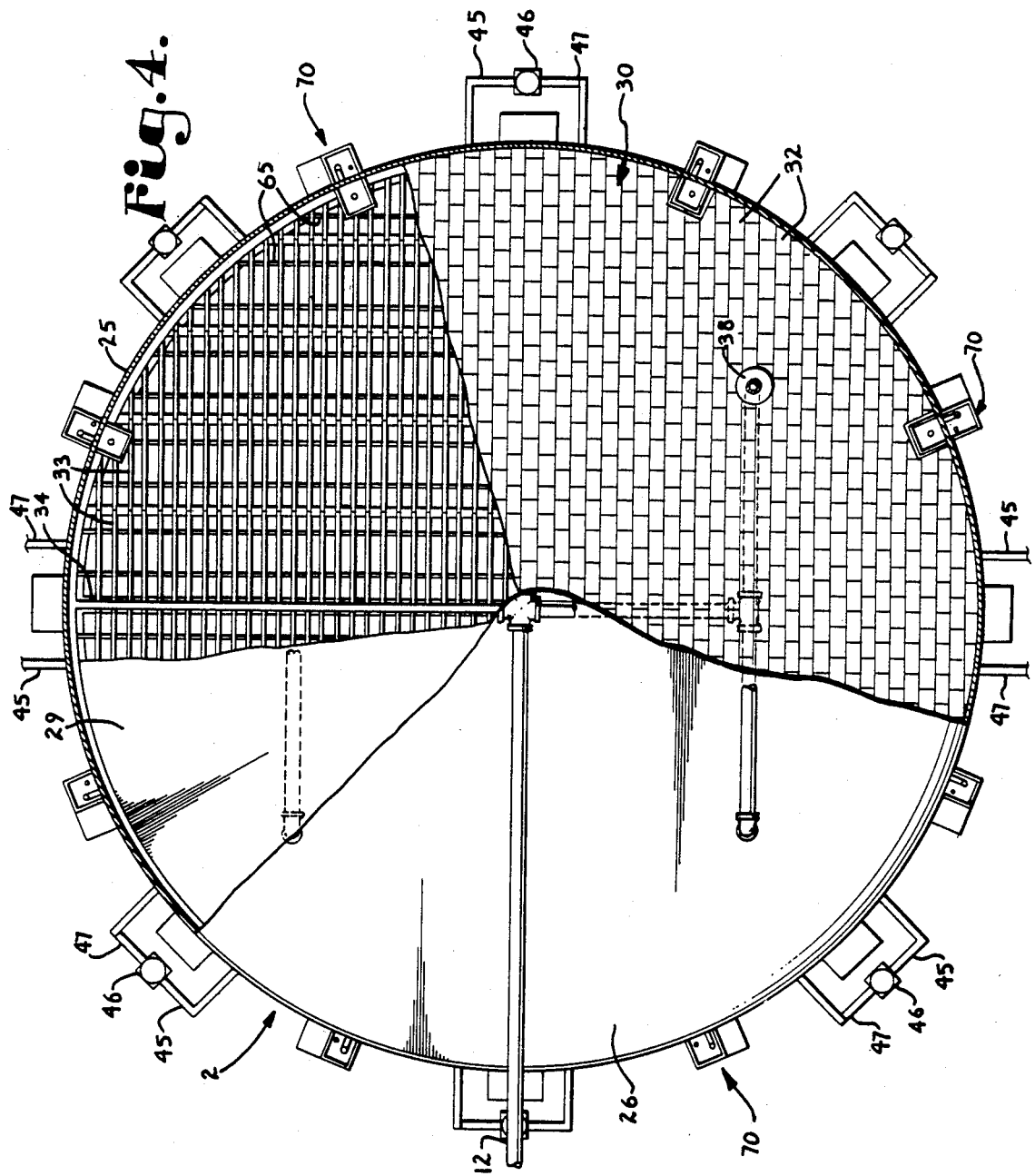
FIG. 4 is a top plan view of the digester with portions broken away at various levels to show details thereof.

An apparatus for treatment of waste water according to the present invention is schematically illustrated in FIG. 1, shown in FIGS. 1 through 6, and is generally referred to by the numeral 1. The apparatus 1 comprises an anaerobic digester 2.

The box 5 generally designates fluid to be treated by the apparatus 1 which may be any waste water solution or the like having organic and/or other contaminants suitable for being acted upon by microorganisms to reduce the amount of organic contamination, especially elements creating an oxygen demand therein. In particular, in the presently described embodiment this fluid is a waste stream of a molasses fermentation and distillation process comprising the non-distilled portion of the fermented molasses, especially carbohydrate residue, less the yeast contained therein. This fluid may also contain other materials such as barrel washings and the like and is generally relatively high in organic substances having a biological and chemical oxygen demand (BOD and COD). The fluid exits the fermentation process at a temperature in the nature of 200 degrees F. and enters a holding tank 7. The holding tank 7 is equipped with agitators (not shown). The fluid from the holding tank 7 is selectively allowed to flow through a conduit 8 and into a pump 9 which is generally a constant volume per unit time pump and thereafter through a conduit 10 under pressure from the pump 9. The fluid then passes through a heat exchanger 11 which may be selectively cooled by a flow stream of fermented molasses prior to distillation thereof or by cooling water from a conventional cooling tower or the like. The fluid may also be selectively heated by the heat exchanger 11. The fluid then passes through the conduit 12 into the digester 2. As better seen in FIG. 2, the conduit 12 diverges into four distribution conduits 13 which enter the digester 2 at somewhat symmetrically spaced locations.

The box 18 generally represents input of phosphorous in a usable form for growth development of microorganisms of the anaerobic methane producing or chemically reducing type. A suitable phosphorous form would be diammonium phosphate as fed to the process by a conventional system well-known in the art. The box 19 generally represents input of nitrogen into the fluid stream which nitrogen is also useful for the growth and development of microorganisms of the type used in the digester 2. A suitable source for the nitrogen may be anhydrous ammonia as provided by a conventional ammonia handling system or alternatively, by use of the ammonium phosphate or the like. It is noted that some fluids may contain a suitable source of phosphorous and nitrogen and thus supplementation thereof will not be necessary.

Preferably a buffering solution is added to the fluid before entry thereof into the digester so that the pH of the fluid entering the digester is in the range of approximately 5 to 9 and preferably between 6.5 and 7.0. As the pH of mostos is approximately 4.5, a basic buffering solution is normally added thereto and is represented by the box 20. The buffering solution should be able to bring the pH of the fluid to the preferred range and maintain same in that range while the fluid is being acted upon by microorganisms in the digester. In particular, bacteria and other microorganisms present in digesters typically first convert the organic material in the fluid stream to an organic acid which, if there is no buffering solution present, will substantially lower the pH of the fluid in the digester. A suitable buffering solution would be caustic soda (sodium hydroxide) or lime, although numerous similar substances may be utilized providing same are compatible with growth of microorganisms in the digester 2. Although not shown, where hydrogen sulfide ion toxicity in the digester 2 is a problem ferric chloride or the like may also added with the buffering solution.

The digester 2 is generally a large cylindrical vessel 25 having a free standing dome 26 which is substantially gas-tight to prevent air from entering the digester 2 and destroying the anaerobic or oxygen-free state therein and to prevent escape of gas to the atmosphere. In the illustrated embodiment, as seen in FIG. 3, a floor 29 of the digester 2 is raised at the center thereof and slopes gradually downwardly toward the outer wall thereof. The interior of the vessel preferably contains a latice, matrix or other suitable media having a substantial surface area thereon. Media 30 should be suitable for retaining and allowing growth of at least a portion of the microorganisms thereon. However, it is important that the flow of the fluid through the digester be somewhat tortuous so as to encourage the fluid to engage and mix with the microorganisms, yet not be impeded. In particular, the path and size of the openings in the media should be of sufficient porosity to allow microorganism biomass which is sloughed from the media 30 to fall or settle in a lower portion of the digester 2 and not plug the flow pathway. Media 30 having openings therein of approximately one inch or slightly greater are considered sufficient. One alternative media 30 would be blocks or bundles 32 of PVC plastic such as sold under the trademarks Vinyl Core and Koro-Z, that is, corrugated polyvinyl chloride assembled into self supporting modules, as manufactured by the B. F. Goodrich Company. In the illustrated embodiment, the bundles 32 of the media 30 substantially fill more than the upper two thirds of the digester 2 up to near the dome 26. The bundles 32 are supported upon cross-members 33 and 34 which are in turn supported by upright stanchions 35 resting upon the floor 29 of the digester 2. There is a substantially open space between the media 30 and the floor 29 such that microorganism biomass sloughed from the media 30 can fall to the floor 29 and be urged outwardly toward the side wall of the digester 2 without interference from the media 30. The fluid entering the digester 2 is preferably evenly distributed by a plurality of radially spaced and horizontally directed nozzles 38 above the media 30.

Recirculation means herein comprising pumps and conduits recirculate fluid from near the floor 29 of the digester 2 to near the top of the media 30. Control means (which could be automatic or manual control valves, a variable speed adjustment on each of the pumps or the like) are utilized to selectively adjust the amount of recirculated fluid passing through the recirculation means per unit time. In particular, in the illustrated embodiment, a plurality of radially spaced conduits 45 are positioned near the lower end of the side wall of the digester 2 and provide for flow of fluid including microorganism biomass or sludge therefrom to an associated pump 46. The pump 46 is an adjustable speed, and thus, fluid displacement pump although it is foreseen that a manual or automatic control valve before or after each pump 46 will provide satisfactory recirculation flow control. The pump 46 recirculates flow through the conduit 47 back into the digester 2 near the top 48 thereof. In the illustrated embodiment there are eight recirculation paths including the conduits 45, 47 and pumps 46. It is desirable to continually and directly recirculate fluid and the microorganism biomass associated therewith from the bottom of the digester 2 to the top thereof such that the biomass is more likely to engage and interact with the digester influent fluid. Such recirculation is also believed to reduce the amount of acidity normally formed near the location where the influent enters the digester 2, as the methane forming bacteria in the biomass can act more quickly. Although the optimum recirculation rate varies substantially between types of fluids and various conditions in the digester 2, a suitable recirculation rate for the presently described process is found to be approximately five times the flow rate of the influent fluid to the digester 2. It has further been found that it is sometimes advantageous to vary the recirculation rate from one portion of the digester as compared to another in order to optimize operation of the digester. As is seen in FIG. 3, the digester 2 is an open vessel which is not segmented into separate compartments. Although the media 30 is placed within the digester 2, there is some horizontal movement of the fluid possible as the fluid passes down through the digester 2 and this is illustrated by the wavy flow lines seen in FIG. 3. The fluid in the digester 2 generally flows in vertically extending and flow interconnected regions, as again is shown by the wavy flow lines, so as to be drawn into one of the recirculation conduits 45 or exit through an outlet. The regions are interconnected to allow flow therebetween and the overall area of a particular region feeding a recirculation conduit 45 may vary as the speed of an associated pump 46 drawing from such region is increased or decreased.

The microorganism utilized in the process may be any microorganism which will convert organic material to methane under anaerobic conditions and the other conditions present within the digester 2. A suitable culture of such microorganisms may be obtained by removing a seed or starter culture from a conventional digester or simply by including a sample of fresh cow manure in the digester during start-up period.

Methane produced within the digester 2 bubbles to the surface of the fluid therein and is collected, along with other gases especially carbon dioxide, within the dome 26 and is conducted therefrom by conduit 53 to a first or low pressure compressor or pump 55 having a preferred outlet pressure of about 17 pounds per square inch. The conduit bifurcates into conduits 56 and 62. At low methane production rates or high methane usage, as discussed below, the methane flows through the conduit 56, which flow is regulated by control valve 63.

Under high methane production and low usage, the methane flows through a second or high pressure compressor or pump 57, having a preferred outlet pressure of about 60 pounds per square inch into a holding tank 54. From the holding tank 64 the methane flows through conduit 64 to join with conduit 56 in conduit 67 after flow is controlled by control valve 61. The methane from conduits 56 and 64 is selectively allowed to flow into conduit 65 by valves 63 and 61 respectively and flow through conduit 65 is further controlled by valve 66. Methane flows through conduit 65 and a desulfurizer 67 when necessary to combustor represented by the box 58 which may be a boiler for producing steam or a heater for distilling the fermented molasses.

It may also be desirable at times to urge a portion of the microorganism biomass from the media 30 as the biomass grows sufficiently large to occlude the passageways through the media 30 or to agitate the biomass within the digester 2. When such occlusion occurs, or when additional scouring of the media 30 is desired, the methane in conduit 56 or in the holding tank 54 may be selectively routed by operation of a valve 68 through conduit 60 under pressure so as to recirculate and enter a lower portion of the digester 2 and be sparged therein by nozzles or apertures along distribution lines 65. The sparged methane tends to loosen, stir and agitate the biomass and urge same to mix or interact with fluid in the digester 2 when the normal rise of methane gas through the media 30 is not sufficient to do so, especially in the vicinity of the digester floor 29.

The tank 54 thereby provides surge for storing excess methane when more is being produced in the digester 2 than is being used in the combustor 58 or being returned to the digester 2. The valves 61, 63 and 66 allow control of the pressure in conduit through pressure control devices such as are known in the art when such control is desired.

Although there is a wide range of temperatures within which methane producing microorganisms will function and any of these temperatures are suitable for operation of the present invention, it has been found in the present process that there are two preferred temperature states. The first such temperature state is normally referred to as the mesophillic range around 95 degrees F. and the other is the thermophillic range between approximately 125 degrees to 130 degrees F. Normally the latter range will provide faster methane production.

The digester 2 is also provided with an effluent outflow device 70. The device 70 includes a liquid trap 71 attached to an upper end 72 of the fluid containing portion of the digester 2. Interior of the wall of the digester 2 and communicating with the trap 71 is an open top collection box 73 which in turn communicates with a downcomer conduit 74. While the effluent may be withdrawn from anywhere along the vessel side 25, the inlet to the conduit 74 thus being the normal location of exit of the effluent from the digester 2, is near the digester bottom 29 and near wall 25. The trap 71 overflows into a conduit 75 and thereafter is transferred by a pump 76 or gravity. In the illustrated embodiment the effluent is wasted to a sewer or the like as represented by box 78 or may be recirculated through a valve 77 and the conduit 60 to the bottom of the digester to agitate the biomass therein.

Thus, in the present embodiment fluid flows into the digester 2 near the top thereof, flows downwardly through the media 30, is recirculated by the recirculating means directly from near the bottom of the digester 2 to near the top thereof at a rate substantially greater than the influent rate, and is removed from the digester 2 after treatment by the microorganisms to reduce oxygen demand in the effluent and to produce methane.

The desulfurizer 67 is positioned such that methane can be selectively routed therethrough when valves 85 and 86 are opened or bypassed when valves 85 and 86 are closed and valves 87 and/or 61 are open. The desulfurizer 67 is of a conventional type suitable for removal of hydrogen sulfide from a gaseous stream, here mostly methane. The desulfurizer 67 is also positioned so that methane can be withdrawn from the digester 2 through conduit 53 and compressor 55 and thereafter directed through a methane recirculation system further comprising conduit 60 to return to near the bottom of the digester 2 when valving is properly adjusted.

In use the method of utilizing the apparatus 1 comprises distributing the influent fluid to be treated near the top of the digester 2, flowing the fluid downwardly through the media 30 so as to contact microorganisms attached to and in the vicinity of such media, recirculating a portion of the fluid from a lower portion of the digester 2 beneath the media 30 directly to an upper portion of the digester 2 near the location of the distribution of the influent therein, and removing an effluent portion of the fluid from the digester 2 such effluent having been substantially treated by the microorganisms so as to remove methane therefrom and to reduce the biological oxygen demand thereof. The recirculation rate may be varied to take advantage of conditions within the digester or to speed flow through certain portions of the digester to dislodge blockage therein.

Preferably, the effluent into the digester 2 is buffered so as to maintain a pH in the nature of 6.5 to 7 with the effluent of the digester desired to be within the range of pH of 6 to 9. Nutrients are added to the influent to optimize growth of the bacteria in the digester 2. Also preferably the digester is maintained at a temperature of optimum growth and therefore activity by the microorganisms. Although such temperature varies somewhat, a suitable temperature has been found to be 95 degrees or alternatively within the range of 125 degrees to 130 degrees F. Gas from the conduit 56 or alternatively from the methane holding tank 54 is diverted to the bottom of the digester 2 and bubbled up therethrough, when it is desired to remove additional biomass from the media 30 or to agitate the biomass to improve interaction with the fluid in the digester 2.

When sulfur buildup within the digester 2 results in "sulfide" poisoning of the microoganisms therein, methane drawn from the top of the digester 2 through the compressor 55 may be partially or totally routed through the desulfurizer 67 and returned to be spraged into the fluid near the bottom of the digester 2. In this manner, the methane passes through the fluid in the digester, partially stripping sulfur containing gasses (hydrogen sulfide) therefrom and passes through the desulfurizer 67 so as to allow removal of the sulfur from the methane which may then be returned to the digester 2 to strip additional sulfur therefrom. The ratio of methane being returned to the digester 2 as compared to that sent to the combuster 58 or storage may be relatively high, especially several multiples of the latter amount when the stripping operation is being utilized to remove sulfur.

It is foreseen that additional treatment may be provided for the effluent of the digester 2 to remove additional contaminants from the waste water. It is also foreseen that the effluent or another liquid instead of the methane gas mixture may be recycled under high pressure to the bottom of the digester to agitate the biomass.

The following examples are included for purpose of illustration only and are not intended to be limiting with reference to the present invention.

EXAMPLE I

The following is a calculated example of the effects of the process disclosed in the preferred embodiment:

| | |
|---|---|
| Influent flow rate of mostos to digester in gallons per day | 340,000 |
| BOD in grams per liter | 47 |
| COD in grams per liter | 92 |
| Pressure in digester in pounds per square inch | 1 |
| pH of mostos before process | 4.5 |
| pH of mostos after addition of NaOH | 7.0 |
| Temperature in digester (degrees Fahrenheit) | 95 |
| Height of digester in feet at side | 40 |
| Height of media in feet | 30 |
| Diameter of digester in feet | 120 |
| Loading of BOD on media in pounds per day per 1000 cubic feet of media | 400 |
| Recirculation rate with respect to flow of influent | 5 |
| Loading of fluid at top of media (influent plus recirculation) in gallons per minute per square foot | 0.13 0.13 |
| Methane production in cubic feet per day | 780,000 |
| COD in effluent in grams per liter | 32 |
| BOD in effluent in grams per liter | 14.1 |
| Biological solids in effluent in pounds per day | 16,000 |

EXAMPLE II

A tank holding 2,300 gallons of fluid when substantially filled with media is maintained at 98 degrees and a pH in the range of 5 to 8, preferably 6.5 to 7.5. Mostos is added at a rate in the range of 115 to 460 gallons per day after neutralization by lime, sodium carbonate, sodium bicarbonate and/or sodium hydroxide. Nutrients, particularly nitrogen and phosphorous from a suitable source, may be added if the mostos is too deficient in such elements to support digester microorganism growth. The recirculation rate is in a range of from 1 to 10 times the rate of addition of mostos to the tank. The recirculation rate is preferentially adjusted to take advantage of conditions within the digester and may vary between different recirculation devices to take advantage of conditions which vary within different portions of the digester. Influent BOD is 25,000 to 45,000 parts per million (ppm) and COD is 70,000 to 110,000 ppm. Retention time varies in the range of 5 to 20 days, preferably 7 days. It is calculated that BOD removal is 60 to 95 percent, COD removal is 60 to 90 percent, and methane gas generation is 4 to 10 cubic feet per pound of COD removed.

EXAMPLE III

The same conditions and results as in Example II except temperature is maintained in the range of 120 degrees to 130 degrees F. and retention time is generally from 2 to 20 days, preferably about 5 days.

DESCRIPTION OF THE SECOND EMBODIMENT

FIGS. 7 through 9 show a modified embodiment of a digester system and apparatus 100 which is generally similar to the apparatus 1 except where described as being different as follows. The apparatus 100 comprises a digester 102 having a media fill 103 including voids and passageways therethrough to allow flow of fluid through the digester 102 and to support microorganism growth thereon.

The digester 102 includes a feed or raw waste supply line 105 with multiple outlets 106 positioned above the media fill 103. The digester 102 also includes multiple overflow outlets 110 which draw fluid from near the bottom of the digester 2 for discharge.

Multiple recirculation means, in the present embodiment, pumps 112, are provided at circumferentially spaced locations about the exterior of the digester 102. In particular, eight pumps 112 are provided at equally spaced positions.

Each pump 112 has a suction conduit 113 and a discharge conduit 114. Each discharge conduit 114 opens into the top of the digester 102 above the media fill 103. As shown in FIG. 7, each discharge conduit 114 has a tail piece 115 which projects inwardly from a side 120 of the digester 102 and is in a generally horizontal plane but angled at approximately 45 degrees to a tangent associated with the digester side 120. Each tail piece 115 is angled to deflect flow of fluid therefrom so as to urge a clockwise rotation of the fluid when viewed from above so as to somewhat agitate the fluid in the top of the digester 102.

The pump suction conduit 113 is formed from the convergence of three intake lines 125, 126 and 127 each having respective intakes or inlets 130, 131 and 132 and respective flow control devices or valves 135, 136 and 137.

The intake lines 125, 126 and 127 are each of such a length to allow radial spacing of the inlets 130, 131 and 132 across the bottom of the digester 102. Various sample ports (too small and numerous to be shown in the figures are pre-positioned at horizontally and circumferentially spaced locations around the digester side 120 and on the intake lines 125, 126 and 127 to allow sampling of fluid at various locations throughout the interior of the digester 102 and the intake lines 125, 126 and 127.

In operation the apparatus 100 works essentially as the apparatus 1 with the following additional description of operation. The operator of the digester 102 may occasionally on a predetermined schedule sample the fluid in the digester 102 at different locations and/or in the intake lines 125, 126 and 127 to determine activity within the media fill 103 associated with such locations by determining the relative amount of undigested material remaining in such fluid. The operator may then adjust the flow through the various pump intake lines 125, 126 and 127 by manipulation of the valves 135, 136 and 137 and/or adjustment of the pump 112 output to optionally direct flow of fluid through the media fill 103 to areas or regions therein where activity is greatest.

Flow through intake lines 125, 126 and 127 can be adjusted to modify the flow radially (adjacent flow through intake lines 125, 126 and 127 associated with a particular pump 112 relative to one another by adjustment of valves 135, 136 and 137) or circumferentially (by increasing or decreasing the total flow going to a particular pump 112 relative to an adjacent pump 112 or even non-adjacent pumps 112).

In this manner flow of fluid to be treated can be selectively reduced through low activity locations in the digester 102 and flow through high activity regions can be increased. The overall total recirculation rate can be adjusted to also maximize activity, but it is noted that the recirculation rate through individual pumps 112 may or may not be the same.

It is to be understood that while certain embodiments of the present invention have been described and shown herein, it is not to be limited to specific forms or arrangement of parts herein described and shown.

What is claimed and desired to secure by Letters Patent is:

1. An apparatus for the treatment of waste water containing oxygen demanding organic material with microorganisms; said apparatus comprising an anaerobic digester; said digester comprising:
   (a) a substantially gastight vessel having a waste water inlet located in an upper portion of said vessel and a treated waste water outlet drawing from a lower portion of said vessel such that said waste water generally flows downwardly through said vessel while therein; said vessel having fluid vertically extending flow interconnected regions such that said fluid can selectively flow through and between said interconnected regions over substantially the entire height of said vessel;
   (b) a plurality of recirculation devices having intakes at spaced locations in said vessel lower portion; each of said recirculation devices being associated with a respective one of said interconnected regions so as to allow withdrawal of a substantial amount of the waste water in said lower portion of said digester from said spaced locations therein and returning the withdrawn waste water directly to said upper portion of said vessel such that microorganisms and the oxygen demanding organic material in said withdrawn waste water may be withdrawn from more than one of said flow interconnected regions simultaneously and thereafter returned to said vessel upper portion;
   (c) each recirculation device including multiple recirculation intakes drawing from radially spaced locations near the digester bottom and control means to selectively vary the flow of recirculated waste water through each of said intakes relative to one another; and
   (d) a high surface area porous media filling at least a medial portion of said digester and suitable for support of microorganism growth thereon; said recirculated waste water being withdrawn through said intakes from spaced locations in said digester beneath said media; said media being located such that said waste water flows downwardly therethrough and engages said microorganisms thereon.

2. The apparatus according to claim 1 including:
   (a) distribution means adapted for distributing an agitation agent under pressure in said digester lower portion so as to agitate a biomass formed by the microorganisms and to thereby improve interaction of the biomass with the oxygen demanding organic material.

3. The apparatus according to claim 2 wherein:
   (a) said microorganisms produce methane during interaction with said fluid; and including:
   (b) gas collection means for removing said methane from said digester; and wherein
   (c) said methane is said agitation agent; and
   (d) said distribution means includes conduit for conveying said methane from said collection means to said digester lower portion.

4. The apparatus according to claim 1 including:
   (a) a methane recirculating system cooperating with said digester and including means to allow selective removal of methane from the top of said digester and return of methane to the bottom of said digester;
   (b) said system further including a desulfurizer positioned to allow selective operative flow therethrough of the methane taken from the top of the digester and returned to the bottom of said digester so as to remove sulfur therefrom.

5. The apparatus according to claim 1 wherein:
   (a) said recirculation devices are sized in combination to provide an amount of recirculation flow of waste water from the lower portion of said digester approximately from one to ten times as great as the flow rate of the waste water through said digester inlet.

6. The apparatus according to claim 1 wherein:
   (a) each of said recirculation devices comprises a pump having a suction conduit communicating with liquid in said digester lower portion at a plurality of said intakes;
   (b) each of said intakes associated with a single pump are generally radially spaced from each other along the bottom of said digester beneath said media and each pump has an intake positioned at approximately equal radial spacings from the outer wall of the digester relative to a similar such spaced intake on each other pump; and
   (c) each intake at such a particular radial spacing is approximately equally spaced from similarly radially positioned intakes of adjacent pumps associated therewith and generally spaced circumferentially about said digester lower portion.

7. The apparatus according to claim 1 wherein:
   (a) said control means comprises control valving to selectively vary the flow of fluid through each individual intake and restrictive means to allow selective overall control of flow of fluid through each of said recirculation devices.

8. The apparatus according to claim 1 wherein interaction of said waste water and said microorganisms produces methane and including:
   (a) collection means for withdrawing said methane from said digester; and
   (b) distribution means located near a floor of said digester and communicating with said collection means so as to selectively return a portion of said methane to said digester lower portion under pressure so as to agitate biomasses formed by said microorganisms thereby facilitating interaction of said microorganisms with said waste water.

9. An apparatus for reducing oxygen demand of a fluid flowing therethrough by activity of microorganisms producing methane from matter in the fluid including:
   (a) a substantially airtight digester having an inlet for adding additonal fluid near a top of the digester and an outlet for drawing fluid with reduced oxygen demand from near a bottom of the digester such that fluid flows generally downward through said digester; said digester having a plurality of flow interconnected regions such that fluid may freely flow therebetween over substantially the entire height of said digester between said interconnected regions as fluid flows downwardly through said digester;
   (b) porous structural media within said digester adapted for supporting growth of the microorganisms thereon and allowing flow of the fluid therethrough;
   (c) a plurality of controllable flow recirculation devices; one of said recirculating devices having an intake located near a bottom of a respective one of said vessel interconnected regions; each of said intakes being spaced from one another; said recirculation devices having outlet means located near the top of said digester, whereby flow through various interconnected regions of said digester may be selectively controlled;
   (d) collection means for collecting the methane from an upper portion of said digester;
   (e) distribution means substantially uniformly positioned beneath said structural media and adapted to distribute said methane in said digester lower portion beneath said structural media;
   (f) a desulfurizer; and
   (g) a recirculation system including means to selectively recirculate methane from said collection means through said desulfurizer and thereafter return the methane to said distribution means for redistribution within the fluid in said digester.

10. The apparatus according to claim 9 including:
    (a) control means to allow selective distribution of methane through portions of said distribution means under portions of said media wherein increased methane flow is desired.

* * * * *